US011883018B2

United States Patent
Anderson et al.

(10) Patent No.: US 11,883,018 B2
(45) Date of Patent: *Jan. 30, 2024

(54) SUTURING KIT AND PACKAGE

(71) Applicant: Durastat LLC, Exton, PA (US)

(72) Inventors: David Greg Anderson, Moorestown, NJ (US); Mark F. Kurd, Bryn Mawr, PA (US); Jay Tapper, Wayne, PA (US); Jens Johnson, Austin, TX (US)

(73) Assignee: DURASTAT LLC, Austin, TX (US)

( * ) Notice: Subject to any disclaimer, the term of this patent is extended or adjusted under 35 U.S.C. 154(b) by 337 days.

This patent is subject to a terminal disclaimer.

(21) Appl. No.: 17/067,910

(22) Filed: Oct. 12, 2020

(65) Prior Publication Data

US 2021/0022734 A1 Jan. 28, 2021

Related U.S. Application Data

(63) Continuation of application No. 15/697,856, filed on Sep. 7, 2017, now Pat. No. 10,835,236.

(51) Int. Cl.
| | |
|---|---|
| *A61B 17/06* | (2006.01) |
| *A61B 17/04* | (2006.01) |
| *A61B 17/00* | (2006.01) |

(52) U.S. Cl.
CPC .... *A61B 17/06114* (2013.01); *A61B 17/0482* (2013.01); *A61B 17/0483* (2013.01);
(Continued)

(58) Field of Classification Search
CPC .......... A61B 17/0482; A61B 17/06114; A61B 2017/0474; A61B 2017/06057;
(Continued)

(56) References Cited

U.S. PATENT DOCUMENTS

| | | | |
|---|---|---|---|
| 5,078,730 A | 1/1992 | Li et al. | |
| 5,392,917 A * | 2/1995 | Alpern | B65D 77/2056 206/370 |

(Continued)

FOREIGN PATENT DOCUMENTS

| | | |
|---|---|---|
| EP | 1980211 A2 | 10/2008 |
| WO | 9842262 | 10/1998 |
| WO | 2017136025 | 8/2017 |

OTHER PUBLICATIONS

Abreu, S.C. et al; "Use of titanium knot placement device (TK-5) to secure dorsal vein complex during laparoscopic radical prostatectomy and cystoprostatectomy." Urology, vol. 67, Issue 1, pp. 190-194, Jan. 2006; PMID: 16413363. DOI: 10.1016/j.urology.2005.07.047; Abstract.

(Continued)

*Primary Examiner* — Ryan J. Severson
*Assistant Examiner* — Andrew P. Restaino
(74) *Attorney, Agent, or Firm* — Rankin, Hill & Clark LLP

(57) ABSTRACT

A suturing kit includes a suture and a suture holder for holding the suture. The suture has a first end and a second, opposite, end. The suture holder includes an elongated wall defining a suture receiving passage that is elongated along a longitudinal axis and terminates at a suture exit opening. The suture receiving passage has a width at least twice the diameter of the suture and receives the suture such that the suture is folded over forming a half loop section spaced from the suture exit opening. A first second of the suture extends from the half loop section toward the first end and a second section of the suture extends from the half loop section towards the second end. The first section and the second section of the suture within the suture receiving passage are aligned parallel to the longitudinal axis.

11 Claims, 5 Drawing Sheets

(52) U.S. Cl.
CPC ........ *A61B 2017/00561* (2013.01); *A61B 2017/0474* (2013.01); *A61B 2017/06057* (2013.01); *A61B 2017/06095* (2013.01); *A61B 2017/06157* (2013.01)

(58) Field of Classification Search
CPC .......... A61F 2/0095; B65D 1/00; B65D 1/22; B65D 2590/00
See application file for complete search history.

(56) References Cited

U.S. PATENT DOCUMENTS

| | | | |
|---|---|---|---|
| 5,458,609 A | | 10/1995 | Gordon |
| 5,540,704 A | * | 7/1996 | Gordon ............ A61B 17/06066 |
| | | | 606/139 |
| 5,860,992 A | | 1/1999 | Daniel |
| 5,868,762 A | | 2/1999 | Cragg |
| 5,908,428 A | | 6/1999 | Scirica |
| 2002/0147382 A1 | | 10/2002 | Neisz et al. |
| 2003/0236535 A1 | | 12/2003 | Onuki et al. |
| 2004/0006352 A1 | * | 1/2004 | Nobles ............... A61B 17/0057 |
| | | | 606/144 |
| 2004/0034369 A1 | | 2/2004 | Sauer |

OTHER PUBLICATIONS

International Search Report filed in PCT/US2018/049450 dated Dec. 20, 2018, 2 pages.
Supplementary European Search Report filed in EP 18 85 4061 dated Dec. 11, 2020, 9 pages.

\* cited by examiner

SUTURING KIT AND PACKAGE

BACKGROUND

The present disclosure relates generally to surgery and the placement of sutures, and more particularly to devices and methods for suture repair of the tissue.

Surgical closure using sutures is one approach to tissue repair. Oftentimes a needle driver or similar device is used to locate and to pass a suture needle through the tissue to be repaired. The suture needle attaches at one end to a predetermined length of suture, which can be stored in a suture package.

Known suture packages can have a racetrack configuration with narrow passageways configured to receive the suture. In these racetrack shaped suture packages, the suture is wound several times around within the package. Sutures are also packaged in laminate envelopes. Similar to the racetrack shaped suture packages, the suture in the laminate envelopes is also wound several times around itself within the package.

SUMMARY

In view of the foregoing, a suturing kit includes a suture and a suture holder for holding the suture. The suture has a first end and a second, opposite, end. The suture holder includes an elongated wall defining a suture receiving passage that is elongated along a longitudinal axis and terminates at a suture exit opening. The suture receiving passage has a width at least twice the diameter of the suture and receives the suture such that the suture is folded over forming a half loop section spaced from the suture exit opening. A first second of the suture extends from the half loop section toward the first end and a second section of the suture extends from the half loop section towards the second end. The first section and the second section of the suture within the suture receiving passage are aligned parallel to the longitudinal axis.

The suturing kit can be provided with a first needle at the first end of the suture and at least one suturing device having a portion configured to be inserted into a patient during a suture surgical procedure. The suturing device includes a first needle holder configured to hold the first needle. In the suturing kit, the suture can be a double-armed suture having a second needle at the second end of the suture. The kit can include a first suturing device including the aforementioned first needle holder and a second suturing device, which is a separate instrument from the first suturing device, that includes a second needle holder configured to hold the second needle.

DETAILED DESCRIPTION

Figure 1:
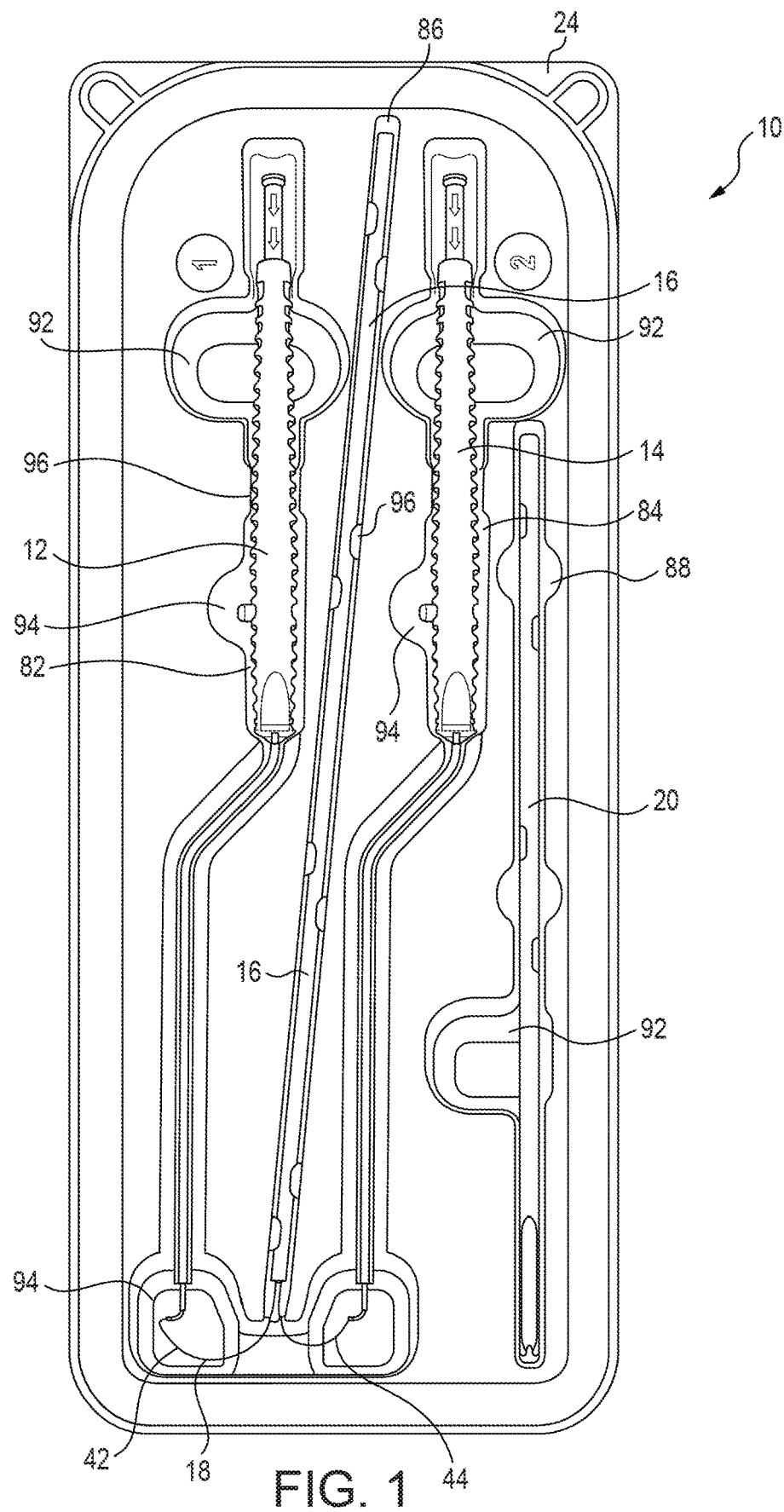
FIG. 1 is a perspective view of a suturing kit including two suturing devices, a suture, a suture holder, and a knot pusher.
Figure 2:
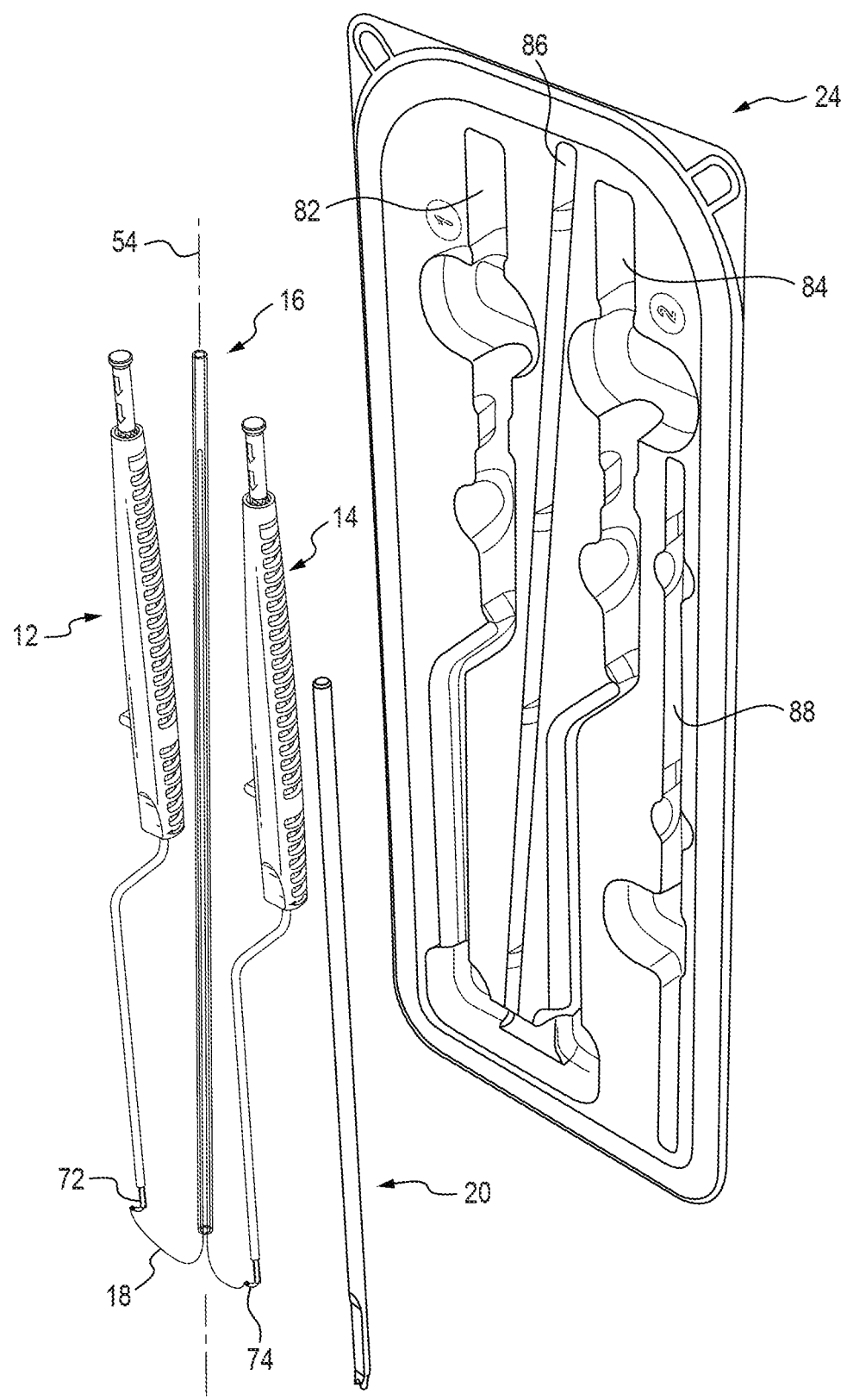
FIG. 2 is a perspective view of the suturing kit of FIG. 1 with the suturing devices, the suture, the suture holder, and the knot pusher removed from a package base.

With reference to FIGS. 1 and 2, a suturing kit 10 includes at least one suturing device (two suturing devices 12, 14 are shown in FIGS. 1 and 2), a suture holder 16, a suture 18, and a knot pusher 20. The suturing devices 12, 14, the suture holder 16, the suture 18, and the knot pusher 20 are received in a package including a package base 24 and are covered by a cover sheet (not shown) similar to a known cover sheet for packaging sterile surgical instruments.

Figure 3:
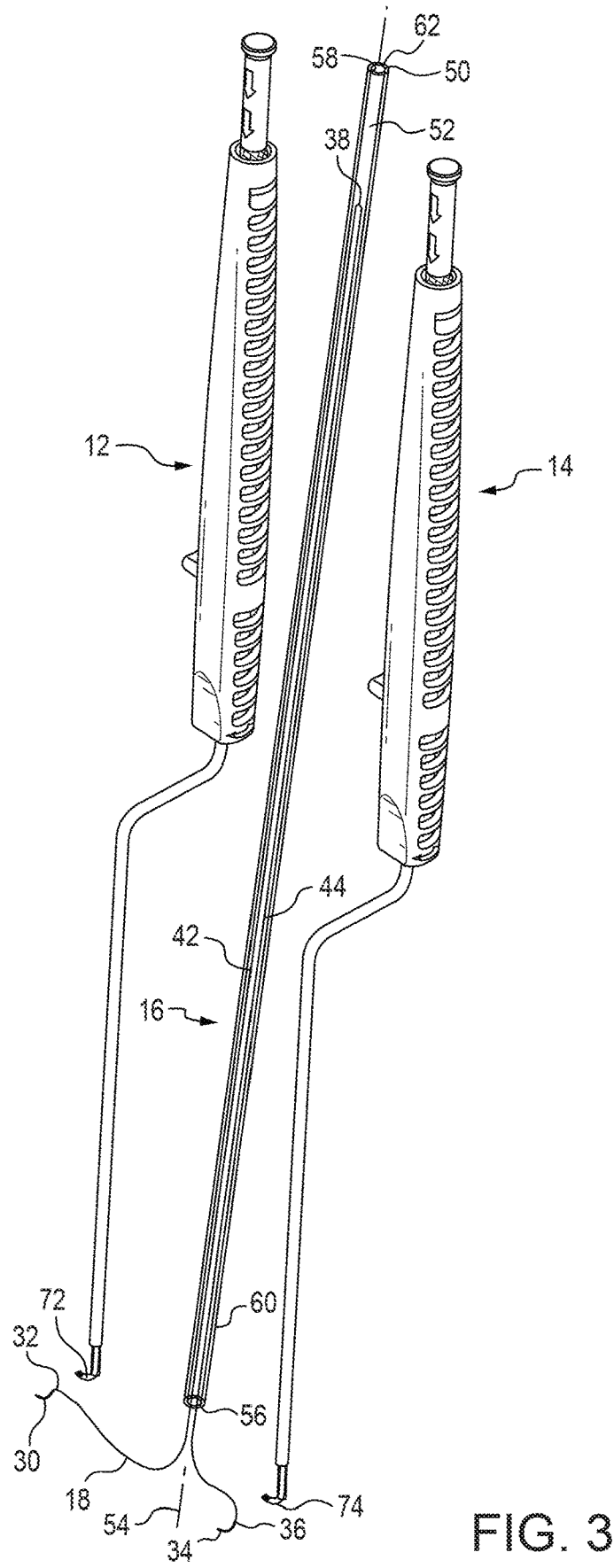
FIG. 3 is a perspective view of the suturing devices and the suture holder with an elongate wall of the suture holder shown as transparent so as to make visible the suture stored therein.

With reference to FIG. 3, the suture 18 has a first needle 30 attached at a first end 32 and a second needle 34 attached at a second, opposite, end 36. The needles 30, 34 can be similar to commercially available curved needles made from known materials. The needles 30, 34 could also be formed from a malleable, or flexible, material such that the needles 30, 34 could follow a curve when positioned within a curved needle holder, and then later straighten after exiting the needle holder. The needles 30, 34 can take other configurations, such as straight. Also, the needles 30, 34 could be formed as part of the suture 18, e.g., the needles 30, 34 could be a rigid end of the suture 18 that is configured so as to be suitable to pass through animal tissue. The suture 18 depicted in FIGS. 1-3 is a double-armed suture having a respective needle 30, 34 at both ends; however, the suture holder 16 can also be used with single-armed sutures.

With reference to FIG. 3, the suture holder 16 is shown as transparent so that the suture 18 received within the suture holder 16 is visible. The suture 18 is doubled over within the suture holder 16 to provide a half loop section 38. A first section 42 of the suture 18 extends from the half loop section 38 toward the first end 32. A second section 44 of the suture 18 extends from the half loop section 38 toward the second end 36 of the suture 18. In contrast to known suture packages, the suture 18 within the suture holder 16 is not wound around itself several times.

The suture holder 16 includes an elongate wall 50 defining a suture receiving passage 52 that is elongated along a longitudinal axis 54 and terminates at a suture exit opening 56. The elongate wall 50 has a closed cross section normal to the longitudinal axis 54 in the illustrated embodiment. The elongate wall 50 is circular in cross section normal to the longitudinal axis 54; however, the elongate wall 50 can take other shapes and need not be a closed cross section. For example, the elongate wall 50 may be C-shaped or U-shaped in cross section. The elongate wall 50 also includes an interior surface 58, which can be smooth so as to inhibit the suture 18 from being caught or snagged during its deployment from the suture holder 16. The elongate wall 50 also includes an exterior surface 60, which can also be smooth and parallel or coaxial with the interior surface 58.

The suture receiving passage 52 also terminates at a second opening 62 spaced from the suture exit opening 56 along the longitudinal axis 54. Accordingly, the suture receiving passage 52 extends entirely through the suture holder 16 along the longitudinal axis 54 and has a configuration similar to a conventional drinking straw. The suture receiving passage 52 has a width, which is measured in the plane normal to the longitudinal axis 54 and in the illustrated embodiment is a diameter of the circular cross section, that is at least twice the diameter of the suture 18, which allows the suture receiving passage to receive the suture 18 such that the suture is folded over forming the half loop section 38. The suture receiving passage 52 is longest along the longitudinal axis 54, which is several times greater than the width of the suture receiving passage 52.

With reference to FIG. 3, when the suture 18 is received in the suture receiving passage 52, the suture 18 is folded over forming the half loop section 38, which is spaced from the suture exit opening 56. As illustrated, the first section 42 of the suture 18 from adjacent to the half loop section 38 to the suture exit opening 56 within the suture receiving passage 52 is aligned parallel to the longitudinal axis 54. Similarly, the second section 44 of the suture 18 from adjacent to the half loop section 38 to the suture exit opening 56 within the suture receiving passage 52 is aligned parallel to the longitudinal axis 54. Both the first section 42 and the second section 44 may not be exactly straight, especially since the suture 18 is a thread-like material, so "parallel" includes not only the case where the angle made by either the first section 42 or the second section 44 and the longitudinal axis 54 is 0°, but also the case where the angle is −5 to +5°. Accordingly, each of the first section 42 and the second section 44 of the suture 18 from adjacent to the half loop section 38 to the suture exit opening 56 within the suture receiving passage 52 can be referred to as aligned along the longitudinal axis 54. As illustrated, there is only one point along the suture 18 within the suture receiving passage 52 where the suture is doubled over, which is the half loop section 38.

With reference to FIG. 1, the suture holder 16 is positioned between the first suturing device 12 and the second suturing device 14 when placed in the package base 24. The first section 42 of the suture 18 residing outside of the suture holder 16 extends away from the second section 44 of the suture 18 residing outside of the suture holder 16 when the suturing kit 10 is packaged. This inhibits tangling of the suture 18 when the suturing devices 12, 14 are removed from the package base 24.

The suturing kit 10 includes the suturing devices 12 and 14, which are each configured to be inserted into a patient during a surgical procedure. The suturing devices 12 and 14 depicted in FIGS. 1-3 are more particularly described in U.S. patent application Ser. No. 15/646,521 filed Jul. 11, 2017. Accordingly, the details of the suturing devices 12, 14 have been omitted for the sake of brevity. The first suturing device 12 includes a first needle holder 72, which holds the first needle 30 (FIG. 3). The second suturing device 14 includes a second needle holder 74 that stores the second needle 34. Other types of suturing devices, such as conventional needle drivers, could be provided with the suturing kit 10 in addition to or in lieu of the depicted suturing devices 12 and 14.

With a continued reference to FIG. 2, the package base 24 includes a first suturing device recess 82 that receives the first suturing device 12, a second suturing device recess 84 that receives the second suturing device 14, and a suture holder recess 86 that receives the suture holder 16. The package base 24 also includes a knot pusher recess 88 that receives the knot pusher 20. The suture holder recess 86 is positioned between the first suturing device recess 82 and the second suturing device recess 84. As mentioned above, and with reference to FIG. 1, the first section 42 of the suture 18 residing outside of the suture holder 16 extends away from the second section 44 of the suture 18 residing outside of the suture holder 16 when the first suturing device 12 is received in the first suturing device recess 82, the second suturing device 14 is received in the second suturing device recess 84 and the suture holder 16 is received in the suture holder recess 86.

The package base 24 can be provided with gripping cutouts 92 that extend outwardly from the first suturing device recess 82, the second suturing device recess 84 and the knot pusher recess 88. The gripping cutouts 92 allow for the insertion of fingers to facilitate removal of the suturing devices 12, 14 and the knot pusher 20. Clearance cutouts 94 can also extend outwardly from the first suturing device recess 82 and the second suturing device recess 84 to provide clearance for movable or delicate components of the suturing kit 10. Tabs 96, which extend inwardly into each of the recesses 82, 84, 86, 88 are provided to retain the appropriate component within the appropriate recess.

As more clearly seen in FIG. 1, when the suture holder 16 is received in the suture holder recess 86, the longitudinal axis 54 is at an angle, i.e., not parallel with, a central axis of each handle of the respective suturing devices 12, 14. This allows for a longer suture holder 16 as compared to if the suture holder were aligned exactly parallel with the handle axes. Also, cutouts may not be provided with the suture holder recess 86, since the suture holder 16 may not be removed from the package base 24 during a procedure, but could instead remain inside the suture holder recess 86 as the suture 18 is removed from it. It is also apparent in FIG. 1, indicia, such as numbers "1," "2," can be provide on the package base 26 to provide a clinician direction with regard to which suturing device to use first in a procedure. As mentioned above, a cover can be provided and attached to the package base 26 to provide a sterile package.

The knot pusher 20 depicted in FIGS. 1 and 2 can be similar to known knot pushers.

A method of assembling the suturing kit 10 includes inserting a midsection 100 of the suture 18, which is positioned between the first end 32 and the second end 36 of the suture 18, into the suture receiving passage 52 of the suture holder 16. The suture 18 is then drawn through the suture receiving passage 52 such that the suture 18 is looped over having only one turning point, which coincides with the half loop section 38 showing in FIG. 3, within the suture receiving passage 52. The turning point of the suture 18 is viewable when viewed in a plane coincident with the longest dimension of the suture holder 16. As mentioned above, the first section 42 and the second section 44 may not be exactly straight, especially since the suture 18 is a thread-like material; however, the suture 18 is not wound several times around itself like the suture inside known racetrack shaped suture retainers and known envelopes.

When assembling the suturing kit 10, a vacuum source 102 can be connected with the suture holder 16 to cover or draw air through the suture receiving passage 52 and the second opening 62 to draw the suture 18 through the suture exit opening 56. The suture 18 can be drawn into the suture receiving passage 52 in other manners, for example by using a hook to grab on to the suture and pull it through the suture receiving passage 52. Drawing the suture 18 by connecting the vacuum source 102 in fluid communication with the suture receiving passage 52, however, is preferred.

As mentioned above, the suture 18 can be a double-armed suture having the first needle 30 connected at the first end 32 and the second needle 34 connected at the second end 36. The suturing kit 10 can be further assembled by loading the first needle 30 in the first suturing device 12 and loading the second needle 34 into the second suturing device 14, which can be performed before or after inserting the midsection 100 of the suture 18 into the suture receiving passage 52 of the suture holder 16 and drawing the suture 18 into the the suture receiving passage 52.

Figure 5:
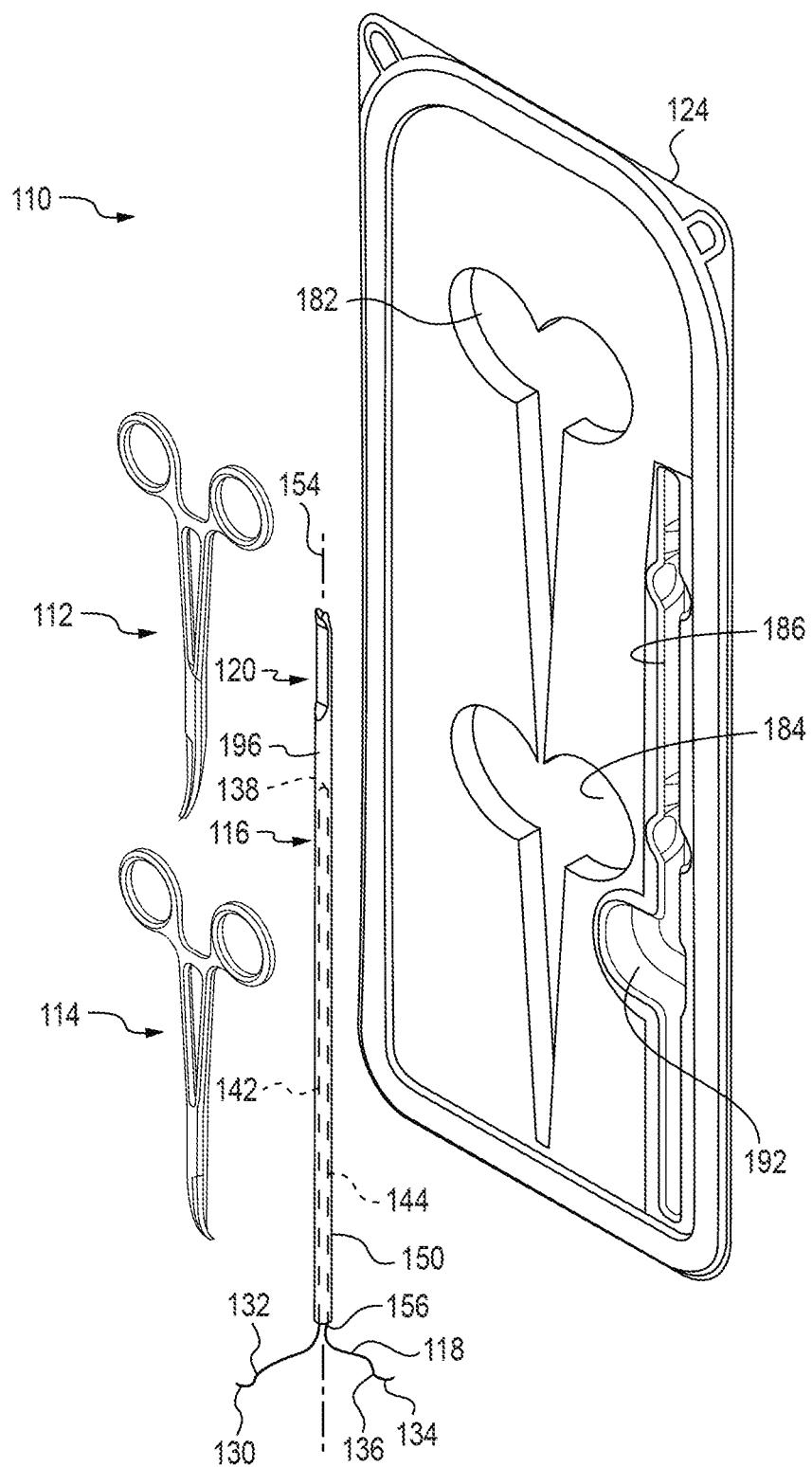
FIG. 5 is a perspective view of an alternative suturing kit.

With reference to FIG. 5, an alternative suturing kit 110 includes at least one suturing device (two suturing devices 112, 114 are shown), a suture holder 116, a suture 118, and a knot pusher 120. The suturing devices 112, 114, the suture holder 116, the suture 118, and the knot pusher 120 are received in a package including a package base 124 and are covered by a cover sheet (not shown) similar to a known cover sheet for packaging sterile surgical instruments.

The suture 118 has a first needle 130 attached at a first end 132 and a second needle 134 attached at a second, opposite, end 136. The needles 130, 134 can be similar the needles 30, 34 described above. The suture 118 depicted in FIG. 5 is a double-armed suture having a respective needle 130, 134 at both ends; however, the suture holder 116 can also be used with single-armed sutures.

The suture 118 (shown in phantom inside the suture holder 116) is doubled over within the suture holder 116 to provide a half loop section 138. A first section 142 of the suture 118 extends from the half loop section 138 toward the first end 132. A second section 144 of the suture 118 extends from the half loop section 138 toward the second end 136 of the suture 118. In contrast to known suture packages, the suture 118 within the suture holder 116 is not wound around itself several times.

The suture holder 116 includes an elongate wall 150 defining a suture receiving passage (similar to the suture receiving passage 52 described above) that is elongated along a longitudinal axis 154 and terminates at a suture exit opening 156. The elongate wall 150 has a closed cross section normal to the longitudinal axis 154 in the illustrated embodiment. The elongate wall 150 is circular in cross section normal to the longitudinal axis 154; however, the elongate wall 150 can take other shapes and need not be a closed cross section. The elongate wall 50 also includes an interior surface, which can be smooth so as to inhibit the suture 118 from being caught or snagged during its deployment from the suture holder 116. The elongate wall 150 also includes an exterior surface, which can also be smooth and parallel or coaxial with the interior surface.

The suture receiving passage also terminates at a second opening, which is covered by the knot pusher 120 in FIG. 5, spaced from the suture exit opening 156 along the longitudinal axis 154. The suture receiving passage has a width, which is measured in the plane normal to the longitudinal axis 154 and in the illustrated embodiment is a diameter of the circular cross section, that is at least twice the diameter of the suture 118, which allows the suture receiving passage to receive the suture 118 such that the suture is folded over forming the half loop section 138. The suture receiving passage is longest along the longitudinal axis 154, which is several times greater than the width of the suture receiving passage.

When the suture 118 is received in the suture receiving passage, the suture 118 is folded over forming the half loop section 138, which is spaced from the suture exit opening 156. As illustrated, the first section 142 of the suture 118 from adjacent to the half loop section 138 to the suture exit opening 156 within the suture receiving passage is aligned parallel to the longitudinal axis 154. Similarly, the second section 144 of the suture 118 from adjacent to the half loop section 138 to the suture exit opening 156 within the suture receiving passage is aligned parallel to the longitudinal axis 154. Both the first section 142 and the second section 144 may not be exactly straight, especially since the suture 118 is a thread-like material, so "parallel" includes not only the case where the angle made by either the first section 142 or the second section 144 and the longitudinal axis 154 is 0°, but also the case where the angle is −5 to +5°. Accordingly, each of the first section 142 and the second section 144 of the suture 118 from adjacent to the half loop section 138 to the suture exit opening 156 within the suture receiving passage can be referred to as aligned along the longitudinal axis 154. As illustrated, there is only one point along the suture 118 within the suture receiving passage 152 where the suture is doubled over, which is the half loop section 138.

The suturing kit 110 includes the suturing devices 112 and 114, which are each configured to be inserted into a patient during a surgical procedure. The suturing devices 112 and 114 depicted in FIG. 5 are similar to needle drivers shaped similar to a hemostat. Other types of suturing devices, such as other conventional needle drivers, could be provided with the suturing kit 110 in addition to or in lieu of the depicted suturing devices 112 and 114.

The package base 124 includes a first suturing device recess 182 that receives the first suturing device 112, a second suturing device recess 184 that receives the second suturing device 114, and a suture holder recess 186 that receives the suture holder 116. The package base 124 can be provided with a gripping cutout 192 that extends outwardly from the knot pusher recess 188. The gripping cutout 192 allows for the insertion of fingers to facilitate removal of the suture holder 116 and the knot pusher 120.

Figure 4:
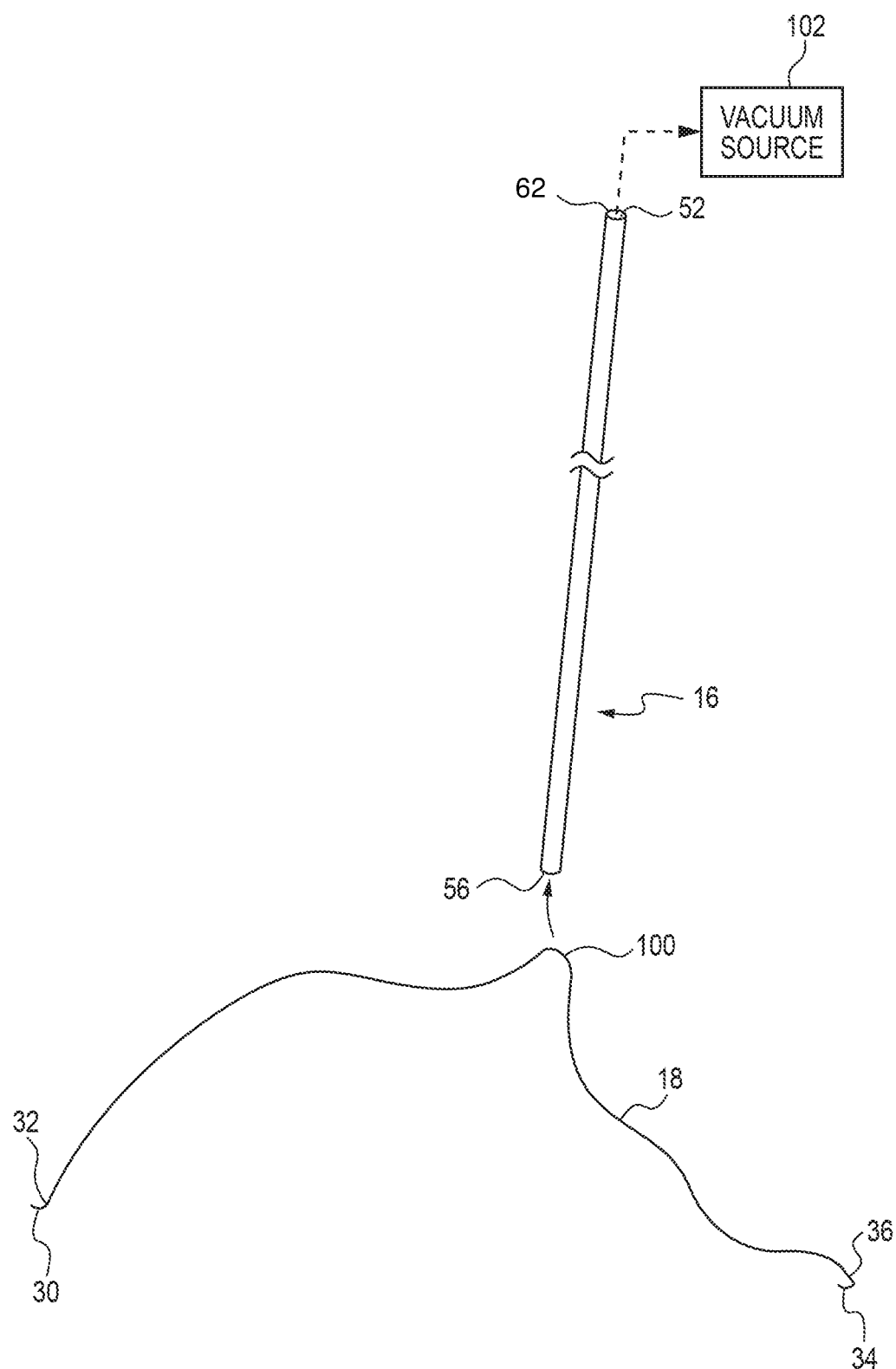
FIG. 4 is a schematic depiction of the suture holder connected with a vacuum source prior to the suture being received in the suture holder.

The knot pusher 120 depicted in FIG. 5 connects with the suture holder 116. As illustrated, the knot pusher 120 connects with an end 196 of the suture holder 116 opposite from the suture exit opening 156. The knot pusher 120 can snap into the opening provided at the end 196 after the suture 118 has been sucked into the suture passage, for example through the use of the vacuum source 102, which is shown in FIG. 4.

Suturing kits and a method of assembling a suturing kit have been described above with particularity. Modifications and alterations will occur to those upon reading and understanding the above detailed description. The invention, however, is not limited to only the embodiments described above. Instead, the invention is broadly defined by the appended claims and the equivalents thereof.

The invention claimed is:

1. A suturing kit comprising:
   a package base including a first suturing device recess, a second suturing device recess and a suture holder recess;
   a suture, which is a double-armed suture, having a first end and a second, opposite, end;
   a suture holder received in the suture holder recess, the suture holder including an elongate wall defining a suture receiving passage that is elongated along a longitudinal axis and terminates at a suture exit opening, the suture receiving passage having a width at least twice the diameter of the suture and receiving the suture such that the suture is folded over forming a half loop section spaced from the suture exit opening, a first section extending from the half loop section toward the first end, and a second section extending from the half loop section toward the second end, wherein each of the first section and the second section of the suture from adjacent to the half loop section to the suture exit opening within the suture receiving passage are aligned along the longitudinal axis;
   a first needle at the first end of the suture and a second needle at the second end;
   a first suturing device received in the first suturing device recess, the first suturing device having a portion configured to be inserted into an associated patient during a surgical procedure, the first suturing device including a first needle holder holding the first needle when the first suturing device is received in the first suturing device recess; and a second suturing device received in the second suturing device recess, the second suturing device being insertable into the associated patient during the surgical procedure wholly separate from the first suturing device, the second suturing device including a second needle holder holding the second needle when the second suturing device is received in the second suturing device recess, wherein the suture holder received in the suture holder recess, the suture holder is configured to remain outside the associated patient during the surgical procedure.

2. The suturing kit of claim 1, wherein the suture holder recess is positioned between the first suturing device recess and the second suturing device recess.

3. The suturing kit of claim 2, wherein the first section of the suture residing outside of the suture holder extends away from the second section of the suture residing outside of the suture holder when the first suturing device is received in the first suturing device recess, the second suturing device is received in the second suturing device recess and the suture holder is received in the suture holder recess.

4. The suturing kit of claim 1, wherein the elongate wall has a closed cross section normal to the longitudinal axis.

5. The suturing kit of claim 4, wherein the closed cross section is circular.

6. The suturing kit of claim 1, wherein the suture receiving passage terminates at a second opening spaced from the suture exit opening along the longitudinal axis.

7. The suturing kit of claim 6, wherein the half loop section is located nearer to the second opening as compared to the suture exit opening.

8. The suturing kit of claim 1, wherein the elongate wall includes a smooth interior surface defining the suture receiving passage.

9. The suturing kit of claim 1, further comprising a knot pusher.

10. The suturing kit of claim 9, wherein the knot pusher is connected with the suture holder.

11. The suturing kit of claim 10, wherein the suture receiving passage terminates at a second opening spaced from the suture exit opening along the longitudinal axis and the knot pusher covers the second opening.

* * * * *